(12) United States Patent
Zuker et al.

(10) Patent No.: US 9,326,832 B2
(45) Date of Patent: May 3, 2016

(54) DEVICE FOR MOUNTING AN IMPRESSION CAP ON A TOOTH IMPLANT

(75) Inventors: Arik Zuker, Zürich (CH); Georg Raeber, Allschwil (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 12/996,137

(22) PCT Filed: Apr. 8, 2009

(86) PCT No.: PCT/EP2009/002597
§ 371 (c)(1),
(2), (4) Date: Jan. 7, 2011

(87) PCT Pub. No.: WO2009/146763
PCT Pub. Date: Dec. 10, 2009

(65) Prior Publication Data
US 2011/0129798 A1    Jun. 2, 2011

(30) Foreign Application Priority Data

Jun. 6, 2008   (EP) .................................... 08010314

(51) Int. Cl.
*A61C 8/00*       (2006.01)
(52) U.S. Cl.
CPC ............... *A61C 8/005* (2013.01); *A61C 8/0001* (2013.01)
(58) Field of Classification Search
CPC ............... A61C 8/0048–8/0078; A61C 8/005; A61C 8/0001
USPC ................................ 433/6, 24, 172–176, 213
See application file for complete search history.

(56) References Cited

U.S. PATENT DOCUMENTS

| 5,125,841 | A | | 6/1992 | Carlsson et al. | |
| 5,197,881 | A | * | 3/1993 | Chalifoux | ...................... 433/173 |
| 5,417,570 | A | | 5/1995 | Zuest et al. | |
| 5,816,812 | A | * | 10/1998 | Kownacki et al. | ............. 433/174 |
| 5,829,981 | A | | 11/1998 | Ziegler | |
| 5,904,483 | A | | 5/1999 | Wade | |
| 6,068,478 | A | | 5/2000 | Grande et al. | |
| 6,332,777 | B1 | * | 12/2001 | Sutter | ........................... 433/173 |
| 6,382,977 | B1 | | 5/2002 | Kumar | |
| 2002/0127515 | A1 | * | 9/2002 | Gittleman | ..................... 433/172 |
| 2003/0224328 | A1 | * | 12/2003 | Sapian | .......................... 433/173 |

(Continued)

FOREIGN PATENT DOCUMENTS

| DE | 41 12 178 A1 | 10/1992 |
| EP | 0 879 025 B1 | 1/1997 |

(Continued)

OTHER PUBLICATIONS

Machine Translation of WO 96/29019.*

(Continued)

*Primary Examiner* — Matthew Nelson
(74) *Attorney, Agent, or Firm* — Therese A. Hendricks, Esq.

(57) ABSTRACT

Secondary part for securing an impression cap (72) releasably on a tooth implant (10). The secondary part (40) is secured on the latter by means of a screw connection. The secondary part (40) has elastically deformable spring fingers (44) that cooperate with a wall (76) of the impression cap (72). The wall (76) is dimensionally stable. With a good fit of the impression cap, the device can thus have a slender configuration, such that it is also suitable in particular for use in the front area of the lower jaw.

11 Claims, 7 Drawing Sheets

(56) References Cited

U.S. PATENT DOCUMENTS

| | | | |
|---|---|---|---|
| 2006/0014120 A1* | 1/2006 | Sapian | 433/173 |
| 2006/0217738 A1 | 9/2006 | Tanimura | |
| 2008/0176186 A1* | 7/2008 | Schaub | 433/173 |
| 2009/0123891 A1* | 5/2009 | Rosenberg | 433/174 |
| 2009/0263760 A1* | 10/2009 | Chung et al. | 433/173 |

FOREIGN PATENT DOCUMENTS

| | | | |
|---|---|---|---|
| EP | 1 444 963 B1 | 2/2003 | |
| EP | 1 946 720 A1 | 1/2007 | |
| FR | 2853828 A | 10/2004 | |
| WO | WO 89/06941 A1 | 8/1989 | |
| WO | WO 96/29019 A1 | 9/1996 | |
| WO | WO 9629019 A1 * | 9/1996 | A61C 8/00 |
| WO | WO 01/05326 A1 | 1/2001 | |
| WO | WO 02/17814 A1 | 3/2002 | |
| WO | WO 03/049636 A1 | 6/2003 | |
| WO | WO 2006/101957 A1 | 9/2006 | |

OTHER PUBLICATIONS

Dec. 6, 2010 of the International Preliminary Report on Patentability and English language translation in corresponding PCT/EP2009/002597.

Aug. 26, 2009 EP International Search Report in related Application No. PCT/EP 2009/002597.

* cited by examiner

DEVICE FOR MOUNTING AN IMPRESSION CAP ON A TOOTH IMPLANT

FIELD OF THE INVENTION

The present invention relates to a device for securing an impression cap releasably on a tooth.

BACKGROUND

A device of this kind is known, for example, from the document EP 0 986 343 A and from the corresponding document U.S. Pat. No. 6,332,777 B, FIG. 23 to 27. A secondary part is secured on an implant by means of a screw connection and has a conically tapering head that protrudes from the implant and that has positioning projections and recesses distributed about the circumference. The secondary part is also provided with an annular groove in which an elastically deformable annular holding means of an impression cap engages in the assembled state. The impression cap also has a dimensionally stable wall at a radial distance from the holding means, and, in the assembled state, the impression cap bears with the base surface of said dimensionally stable wall on a peripheral shoulder of the implant. The holding means and the annular groove from a releasable snap-fit connection.

This known device is particularly suitable at locations of teeth of relatively large cross section. However, it is less suitable at locations of teeth of smaller cross section, for example in the front area of the lower jaw, where implants of small cross section often have to be inserted and little space is available.

U.S. Pat. No. 6,382,977 B discloses an impression element that can be fitted with a stub-like projection into the recess of an implant. The projection has spring fingers for securing releasably on the implant with a force fit. In the case of implants of small cross section, this device is unlikely to provide sufficiently reliable stability when taking an impression.

SUMMARY OF THE INVENTION

It is therefore an object of the present invention to make available a device of the type in question which ensures a stable hold of the impression cap on the tooth implant while requiring little space.

According to the invention, an elastically deformable holding means for securing an impression cap releasably on the tooth implant are formed integrally on a secondary part and not, as in previously known devices, on the impression cap. In this way, the impression cap can be provided with a dimensionally stable wall, even in the area in which it cooperates with the secondary part. This permits an extremely stable design of the impression cap, even at extremely small diameters. Securing the impression cap on the tooth implant with a force fit ensures that this securing can be undone, without destruction, by overcoming a predetermined force. A frictional connection and, preferably, a snap-fit connection releasable by tensile force are particularly suitable for the securing.

The device according to the invention permits a stable design of the impression cap without deformable areas. It can simply be pushed in the axial direction over the secondary part secured on the tooth implant or can be axially joined to said secondary part, thus avoiding deformable sections on the outer surface. Stable securing of the impression cap on the tooth implant is permitted even with small diameters. The device is also suitable for the use of closed impression trays.

In a preferred embodiment of the secondary part, a screw connection ensures extremely stable securing of the secondary part on the tooth implant. Moreover, it is possible for a part of the screw connection, preferably a screw shank with external thread, to be formed on the secondary part. However, it is also possible to provide the secondary part with a continuous hole through which a screw can be turned into the tooth implant with internal thread. This permits a precisely defined position of rotation of the secondary part in relation to the tooth implant. The elastically deformable holding means can be formed simply by at least one spring finger.

Particularly stable securing of the impression cap in the tooth implant can be achieved with a particularly preferred embodiment of the device wherein the spring finger has, in its free end area, a snap-in lug that cooperates with an undercut formed on the dimensionally stable wall of the impression cap.

A simple force-fit snap connection that is releasable by tensile force is also provided wherein the spring finger and/or the undercut has a support face extending at an acute angle (a) with respect to an axial joining direction (F) in order to form a snap-fit connection that can be released by pulling.

In a particularly preferred embodiment of the device the secondary part has at least two spring fingers with a snap-in lug that allows symmetrical securing forces to be obtained.

A particularly exact alignment of the axis of the tooth implant and of the secondary part is achieved in a preferred embodiment wherein the base area has a jacket surface which lies free in relation to the tooth implant and on which the dimensionally stable wall of the impression cap bears in an assembled state.

A defined position of rotation of the impression cap relative to the tooth implant can easily be achieved with a preferred embodiment of the device wherein the tooth implant and the secondary part have cooperating first positioning means, and the secondary part and the impression cap have cooperating second positioning means for mutually fixing the position of rotation, in which defined positions of rotation are adopted by the secondary part relative to the tooth implant and by the impression cap relative to the secondary part.

A particularly simple possibility of ensuring a defined position of rotation between secondary part and tooth implant is provided:
  wherein the first positioning means have a stub with a cross section of a regular polygon, and a recess of matching cross section; and
  wherein the cross section is a regular, even-sided polygon.

Particularly preferred embodiments of the device according to the invention for ensuring a defined position of rotation of the impression cap relative to the secondary part are provided:
  wherein the second positioning means have a recess which is formed on the impression cap and is limited in the circumferential direction and with which the holding means of the secondary part engages in an assembled state;
  wherein the impression cap has a recess which is limited in the circumferential direction and with which the spring finger engages in the assembled state in order to fix the mutual position of rotation;
  wherein the impression cap has a recess which is limited in the circumferential direction and with which a snap-in lug of the spring finger engages in an assembled state in order to fix a mutual position of rotation; and
  wherein the undercut is formed on the recess.

A particularly precise transfer of the implant height by the impression cap is ensured in the particularly preferred embodiments of the device according to the invention:

wherein the tooth implant is designed in one piece and has an anchoring portion, which is intended to be inserted in the jaw bone, and a head portion, which is intended to protrude above the jaw bone, and the head portion has a peripheral shoulder, preferably in the shape of the jacket of a truncated cone, on which the impression cap, in an assembled state, bears via a base surface of at least approximately the same shape; and wherein a preferably peripheral support surface is formed on the secondary part, on which support surface the impression cap bears, in the assembled state, via a base surface of at least approximately the same shape.

Preferably, when taking an impression, the following three coordinates, namely angle of the tooth implant (of the axis of the tooth implant), height of the implant relative to the jaw bone or to the adjacent teeth, and position of rotation of the implant, are transferred by means of the device according to the invention to a laboratory model, which is in most cases made of plaster. For this purpose, the impression cap according to the invention is made of a harder material, for example a metal or a metal alloy, in particular titanium or a titanium alloy, than the secondary part, which is made, for example, of a polymer.

The impression cap is preferably pressed in the axial direction against the tooth implant by the forces exerted by the elastically deformable holding means, such that the impression cap lies securely on a defined surface, for example a shoulder of the tooth implant or a support surface of the secondary part. In this way, the height of the tooth implant can be transferred particularly reliably to the laboratory model.

A particularly reliable transfer of the implant axis is ensured by the design of a guide part on the secondary part for the impression cap, for example a jacket surface on which the dimensionally stable wall of the impression cap bears in the assembled state.

The defined position of rotation of the secondary part relative to the implant is preferably ensured by means of a polygonal connection geometry in which the respective geometries of the secondary part and of the implant coincide, and the defined position of rotation of the impression cap relative to the secondary part is preferably ensured by a number of spring fingers, which are designed with snap-in lugs and which engage in recesses of the impression cap.

If the connection geometry is regular and has an even number of corners, the secondary part preferably has half as many spring fingers with snap-in lugs as there are corners in the connection geometry; for example, in an octagonal connection geometry, preferably four spring fingers, each with a snap-in lug. However, the number of spring fingers can also coincide with the number of corners of the connection geometry, or twice as many spring fingers can be provided as there are corners of the connection geometry. Generally speaking, the number of spring fingers should be a multiple or a fraction of the number of positions of rotation that are permitted by the connection geometry.

BRIEF DESCRIPTION OF THE DRAWINGS

The device according to the invention is explained in more detail on the basis of embodiments shown purely schematically in the drawings, in which.

DETAILED DESCRIPTION

Figure 1:
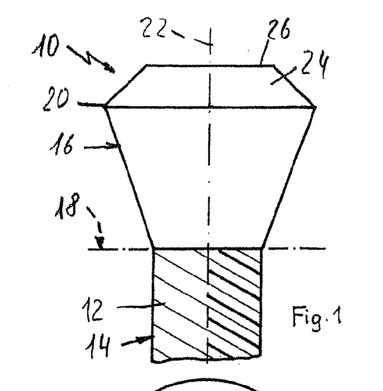
FIG. 1 shows a view of an upper part of a tooth implant.
Figure 2:
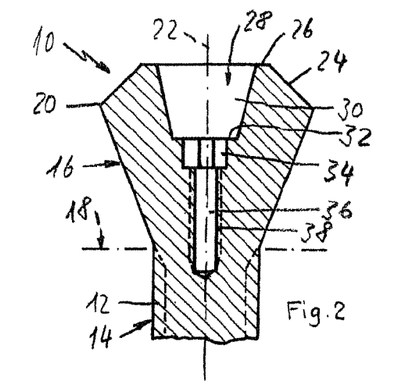
FIG. 2 shows a longitudinal section through the tooth implant according to FIG. 1.
Figures 3, 4, 5, 6, 7:
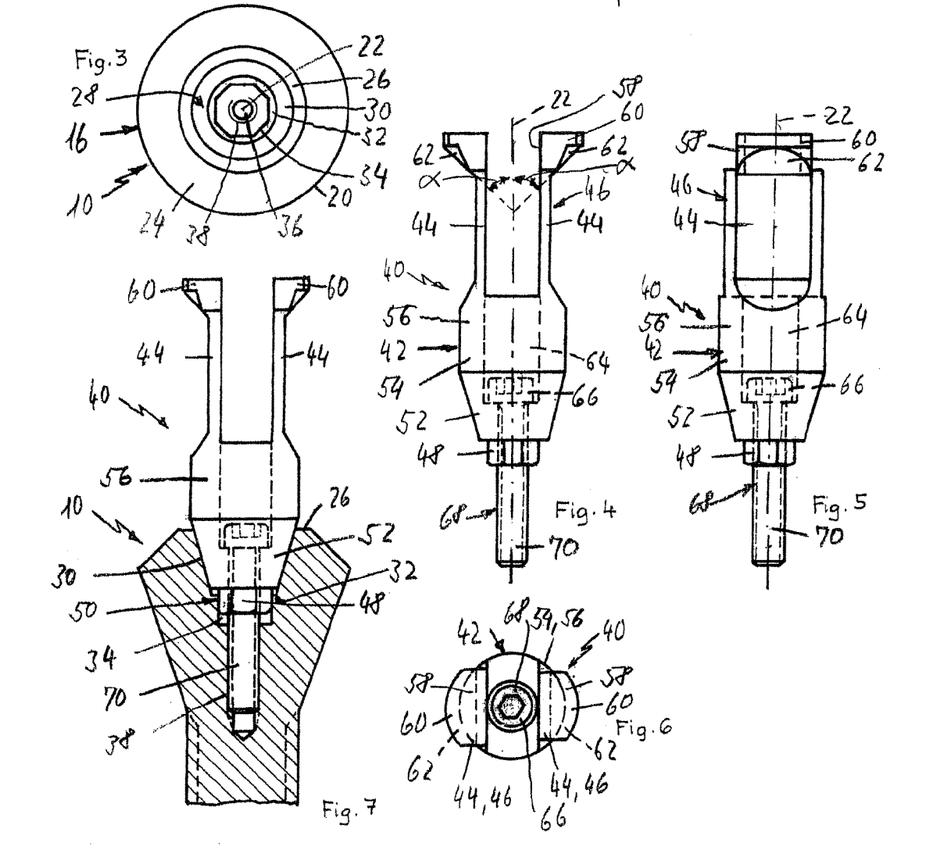
FIG. 3 shows a plan view of the tooth implant according to FIG. 1.
FIG. 4 shows a view of a first embodiment of a secondary part with an implant screw.
FIG. 5 shows a side view of the secondary part according to FIG. 4 with the implant screw.
FIG. 6 shows a plan view of the secondary part and the implant screw according to FIG. 4.
FIG. 7 shows a view of the secondary part according to FIGS. 4 to 6 inserted into the tooth implant, shown in longitudinal section, according to FIGS. 1 to 3 and secured thereon by means of an implant screw.

FIGS. 1 to 3 show schematic views of a tooth implant 10, which has an anchoring portion 14, provided with an external implant thread 12, and a head portion 16 adjoining said anchoring portion 14. The substantially rotationally symmetrical tooth implant 10 is intended to be inserted with its anchoring portion 14 into a jaw bone 18 in a known way, such that it protrudes with its head portion 16 above the jaw bone and passes at least approximately through the mucous membrane. From the direction of the anchoring portion 14, the head portion 16 widens conically to a peripheral outer edge 20 of the implant. The distance between the anchoring portion 14 and the outer edge 20 of the implant, as measured in the direction of the longitudinal axis 22 of the tooth implant 10, preferably corresponds at least approximately to the thickness of the mucous membrane. Following the outer edge 20 of the implant, the head portion 16 tapers conically toward its free end and forms a peripheral shoulder 24 in the shape of the jacket of a truncated cone. On the end face directed away from the anchoring portion 14, the head portion 16 has, adjacent to the shoulder 24, an annular flat end face 26, which is arranged in a plane at right angles to the longitudinal axis 22 and from which an implant recess 28 extends radially inward. This implant recess has, adjacent to the end face 26, a conically tapering portion 30. The bottom 32 of this conical portion 30 is followed by an octagonal portion 34 of the implant recess 28, which octagonal portion 34 is in turn followed by a threaded portion 36 with an internal thread 38. Single-piece tooth implants 10 of this kind are generally known. They are normally made of a metal or a metal alloy, in particular titanium or a titanium alloy.

A first embodiment of a secondary part 40 according to the present invention, suitable for securing on the tooth implant 10 by means of a screw connection 39, is shown in FIGS. 4 to 6. It has a base area 42, which is symmetrical with respect to the longitudinal axis 22, and two spring fingers 44 protruding from this base area 42. The spring fingers 44 extend parallel to the longitudinal axis 22, are arranged diametrically opposite each other in relation to the latter and form elastically deformable holding means 46.

The secondary part 40, which is produced in one piece and preferably from a polymer, has, in its lower end area in FIGS. 4 and 5, a stub portion 48 which is of octagonal cross section and matches the octagonal portion 34 of the tooth implant 10 and is intended to engage in the latter in the assembled state, as is shown in FIG. 7. The octagonal portion 34 of the tooth implant and the correspondingly shaped stub portion 48, which is slightly shorter in the axial direction, fix the mutual position of rotation and form first positioning means 50.

Adjoining the stub portion 48, the base area 42 has a conically widening base position 52. This conical base portion 52 matches the conical portion 30 of the tooth implant 10 and is intended to bear on this conical portion 30 in the assembled state (see FIG. 7). In the assembled state, the base portion preferably protrudes above the end face 26 and does not reach as far as the bottom 32.

The conical base portion 52 is followed, on the side directed away from the stub portion 48, by a guide portion 54 with an outer jacket surface 56 of circular cylindrical shape arranged concentrically with respect to the longitudinal axis 22. The transition from the conical base portion 52 to the guide portion 54 can be made at the end face 26, in the assembled state on the tooth implant 10, but this transition is preferably arranged, in the assembled state, at a distance from the tooth implant 10, as is evident in particular from FIG. 7. In the assembled state, the jacket surface 56 lies free in relation to the tooth implant 10.

The guide portion 54 is followed by the two spring fingers 44, which protrude from the base area 42 in the direction away from the stub portion 48. At their free end area 58, the two spring fingers 44 each have a snap-in lug 60 protruding outward in the radial direction. The snap-in lugs 60 are provided with a support face 62, which extends at an acute angle α to the longitudinal axis 22 and in the present case is designed as part of a cone surface.

A passage 64 for a screw extends all the way through the base area 42 in the direction of the longitudinal axis 22. This passage 64 has a stepped design, so as to provide support for the screw head 66 of an implant screw 68 inserted therein from the direction of the spring fingers 44. The inserted implant screw 68 protrudes with its threaded shank 70 from the secondary part 40 and is intended to cooperate with the internal thread 38 of the tooth implant 10, thus forming the screw connection 39, and to hold the secondary part 40 securely on the tooth implant 10 in the assembled state (FIG. 7).

Figure 8:
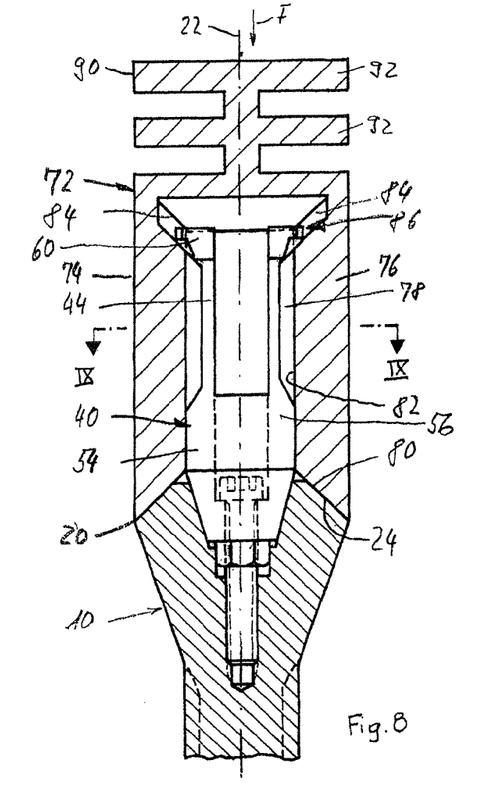
FIG. 8 shows, in the same view as in FIG. 7, the secondary part mounted on the tooth implant, and an attached impression cap likewise shown in longitudinal section.

FIG. 8 shows the device according to the invention with an impression cap 72 mounted in joining direction F on the tooth implant 10, which is provided with the secondary part 40. The joining direction F runs in the direction of the longitudinal axis 22. The entire impression cap 72 is dimensionally stable and is preferably made from a polymer, a metal or a metal alloy. It has a circular cylindrical body portion 74, the external diameter of which coincides with the diameter of the circular outer edge 20 of the implant. With its dimensionally stable wall 76, the body portion 74 peripherally delimits a receiving space 78 in the shape of a blind hole for the guide portion 54 and the spring fingers 44 of the secondary part 40. The end face of the wall 76 is provided with a base surface 80 which matches the shape of the shoulder 24 of the tooth implant 10. In the assembled state, the impression cap 72 bears with the base surface 80 on the shoulder 24 of the tooth implant 10. Moreover, the radially inner surface 82 has a circular cylindrical shape matching the jacket surface 56, so as to bear thereon with a centring effect in the assembled state.

In its end area directed away from the base surface 80, the otherwise circular cylindrical receiving space 78 is widened by two diametrically opposite recesses 84. These recesses 84 are limited in the circumferential direction and have, in the circumferential direction, an extent which, measured in the same direction, corresponds to or is only slightly greater than the extent of the snap-in lugs 60, such that, as a result of the spring action of the spring fingers 44, the snap-in lugs 60 can come into engagement with the recesses 84 when the impression cap 72 is mounted on the tooth implant 10 provided with the secondary part 40. The recesses 84 form, together with the snap-in lugs 60, second positioning means 86 for fixing the position of rotation between the secondary part 40 and the impression cap 72. The recesses 84 also form undercuts 88, and, in the example shown, these undercuts 88 constitute a support face 62' shaped to correspond to the support face 62 of the snap-in lugs 60. The conical support faces 62, 62' forming an acute angle α with respect to the longitudinal axis 22 cause, as a result of the spring action of the spring fingers 44, a force component in the direction of the longitudinal axis 22 with which the impression cap 72 is pressed in the direction against the tooth implant 10, such that it bears with its base surface 80 snugly on the shoulder 24 of the tooth implant. When taking an impression, this allows a very precise copy of the height position of the tooth implant. Moreover, the support faces 62, 62' permit an automatic release of the snap-fit connection 81 and thus of the securing of the impression cap 72 on the tooth implant 10 when a predetermined force counter to the joining direction F is exceeded.

At the end directed away from the base surface 80, the body portion 74 is adjoined by an anchoring zone in which anchoring wings 92 are formed by diametrically opposite slits 92.

The anchoring zone 90 serves to firmly anchor the impression cap 72 in a generally known and hardening impression compound which, as is generally known, is pressed by means of a tray over the impression cap 72 mounted on the tooth implant 10 and, if necessary, over adjacent teeth or impression caps, in order to take an impression of the dentition.

Figure 9:
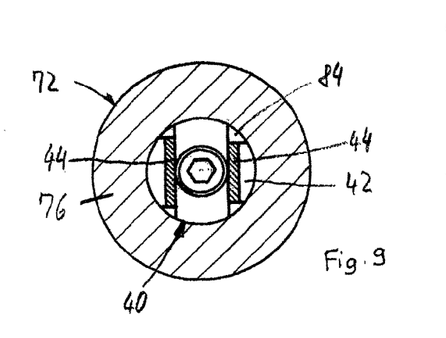
FIG. 9 shows a section along the line IX-IX through the device in FIG. 8.

The cross section of the dimensionally stable wall 76, and the cooperation of the latter with the guide portion 54 of the secondary part 40, is also evident in particular from FIG. 9, in which it can also be seen clearly that the two spring fingers 44 have different widths. The purpose of this design will be described in more detail below in connection with FIGS. 12 to 15. The guide portion ensures a very exact transfer of the longitudinal axis of the tooth implant 10 when taking an impression.

Figure 10:
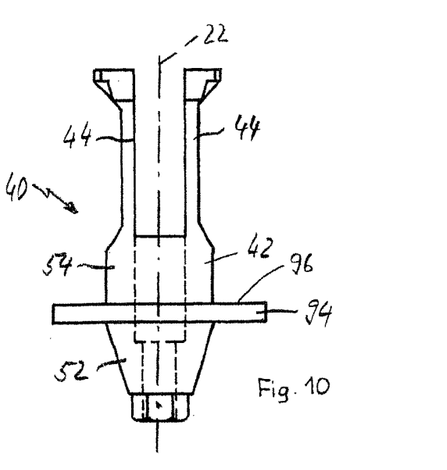
FIG. 10 shows a view of a second embodiment of a secondary part, with an annular support surface for an impression cap.

FIG. 10 shows a second embodiment of the secondary part 40 of a device according to the invention. The only difference in this embodiment from the embodiment described above and shown in FIGS. 4 to 6 is that the base area 42 has, between the conical base portion 52 and the circular cylindrical guide portion 54, a peripheral projection 94 protruding in the radial direction and shaped like an annular disk. This projection forms, with its face directed toward the spring fingers 44, a peripheral support surface 96, which lies in a plane extending at right angles to the longitudinal axis 22.

Figure 11:
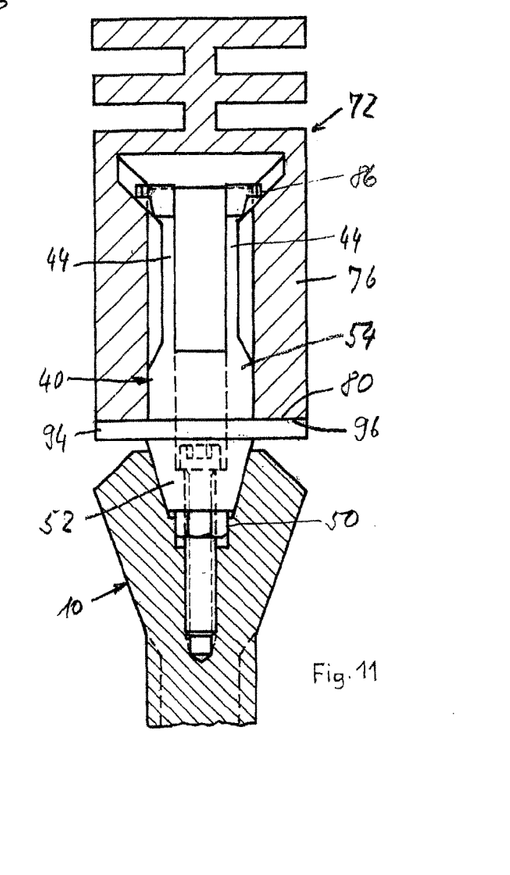
FIG. 11 shows, in the same view as in FIG. 8, the secondary part according to FIG. 10 mounted on the tooth implant, with an attached second embodiment of an impression cap bearing on the support surface.
Figure 12:
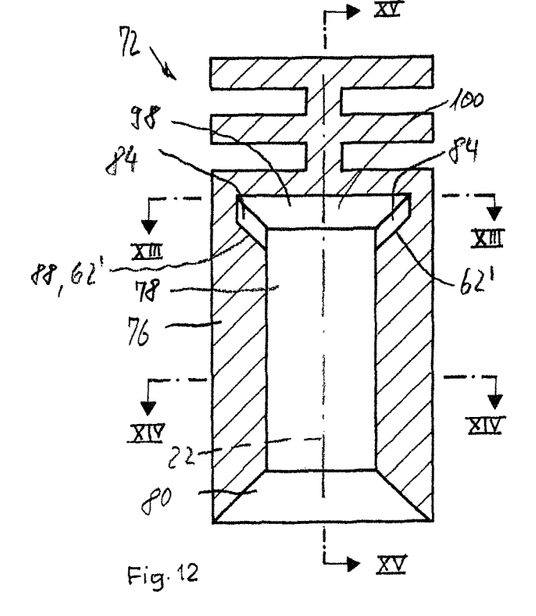
FIG. 12 shows a longitudinal section through the impression cap of the device according to FIG. 8.
Figure 13:
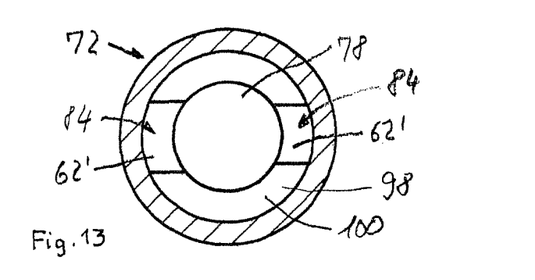
FIG. 13 shows a section through the impression cap along the line XIII-XIII in FIG. 12.
Figure 14:
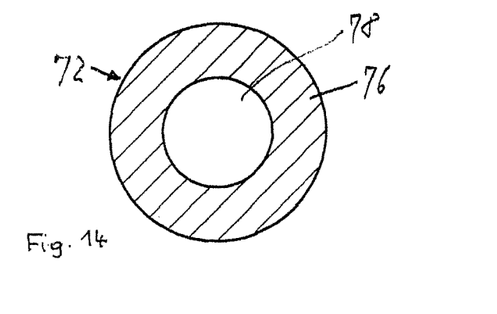
FIG. 14 shows a section through the impression cap along the line XIV-XIV in FIG. 12.
Figure 15:
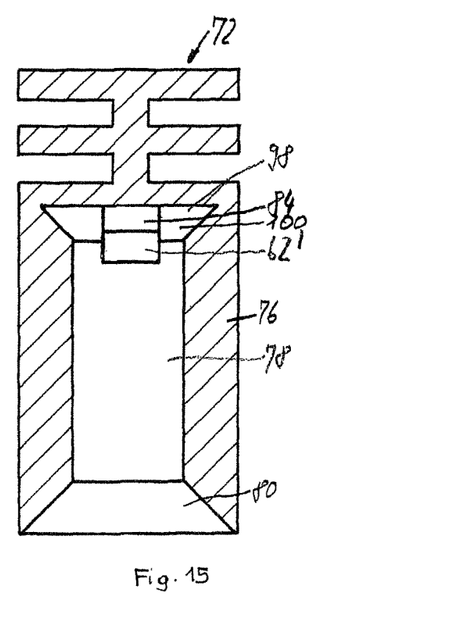
FIG. 15 shows a longitudinal section through the impression cap along the line XV-XV in FIG. 12.
Figure 16:
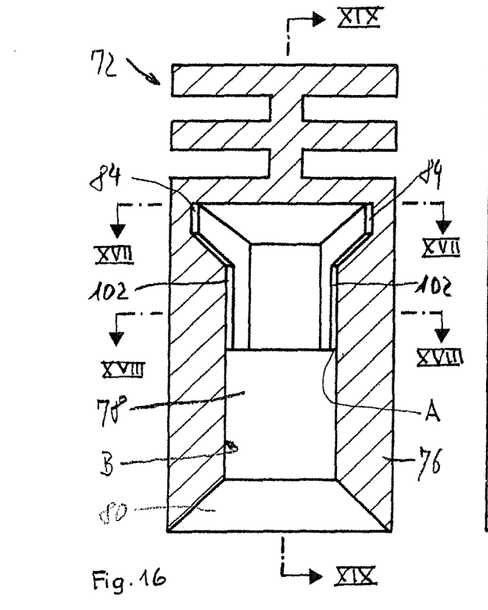
FIG. 16 shows a longitudinal section through a third embodiment of an impression cap.
Figure 17:
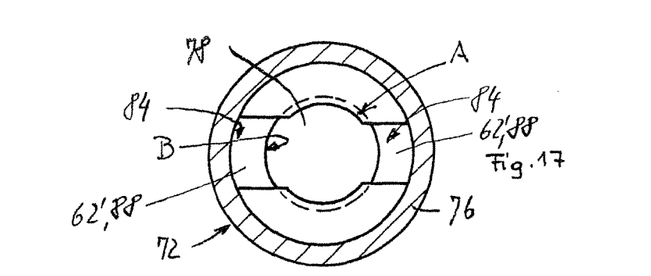
FIG. 17 shows the impression cap in section along the line XVII-XVII in FIG. 16.
Figure 18:
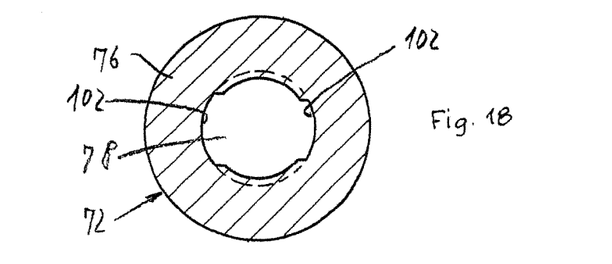
FIG. 18 shows a section through the impression cap along the line XVIII-XVIII in FIG. 16.
Figure 19:
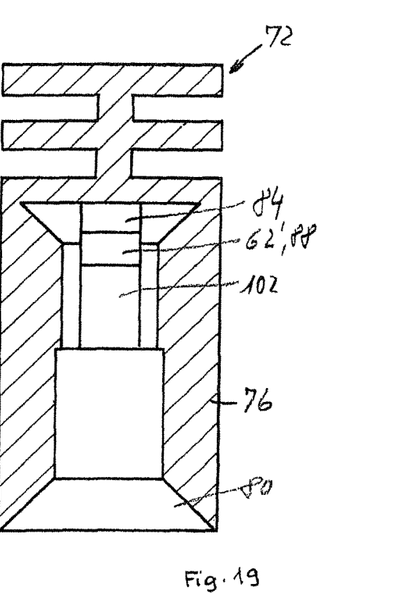
FIG. 19 shows a longitudinal section through the impression cap along the line XIX-XIX in FIG. 16.

FIG. 11 shows a device according to the invention with the secondary part 40 according to FIG. 10 inserted in the tooth implant 10. An impression cap 72 is snapped onto the secondary part 40, which impression cap 72 has the same design as the impression cap 72 shown in FIGS. 8 and 9, except that the base surface 80 is designed as a plane annular surface corresponding to the support surface 96 of the secondary part 40. In the assembled state, the impression cap 72 bears with its base surface 80 on the support surface 96 and, as has been described above, is held in this bearing position by means of the spring fingers 44. Here too, a particularly good centring of the impression cap 72 is ensured by the dimensionally stable wall 76 bearing on the guide portion 54. In this embodiment, the height position of the tooth implant 10 is transferred to the impression, or to the laboratory model, indirectly via the secondary part 40 and the connection thereof to the tooth implant 10. The transfer of the position of rotation takes place exactly in the manner described above, namely via the first and second positioning means 50, 86. The position of the longitudinal axis 22 of the implant 10 is also transferred in the manner described above.

In FIGS. 12 to 15, the embodiment of the impression cap 72 already shown in FIG. 8 is depicted on its own. The relatively thick, dimensionally stable wall 76 of circular cross section can be seen particularly clearly in FIGS. 12, 14 and 15. This wall 76 peripherally delimits the receiving space 78 shaped like a blind hole. This receiving space 78 is widened conically in its closed end area 98 directed away from the base surface 80, the wall 76 forming a cone-shaped slide surface 100. The two recesses 84 with the support faces 62' on the wall 76 are set back axially and radially in relation to this slide surface 100. As can be seen particularly clearly from FIG. 13, the recess shown on the right is narrower in the circumferential direction than the recess 84 shown on the left. Since the spring finger 44 shown on the right in FIGS. 4, 6 and 9 is correspondingly narrower than the spring finger 44 shown on the left, this permits an unambiguous position of rotation of the impression cap 72 relative to the secondary part 40. The spring finger 44 shown on the left in said figures can engage with its snap-in lug 60 only in the recess 84 shown on the left in FIGS. 12 and 13.

When mounting the impression cap 72 on the tooth implant 10 provided with the secondary part 40, the impression cap 72, aligned approximately to the position of rotation of the secondary part 40, is pushed in joining direction F (see FIG. 8) over the secondary part 40, and, as a result of the conical base surface 80, the spring fingers 44 are automatically deflected radially inward. The impression cap 72 is then pressed down until it bears with its base surface on the shoulder 24 of the implant, and, if appropriate, it is turned slightly to and fro until the snap-in lugs 60 of the spring fingers 44 snap into the recesses 84 and thus come into operative engagement with the undercuts 88. This turning to and fro is not necessary if the position of rotation of the impression cap 72 is correct and the spring fingers 44 can engage directly in the recesses, otherwise the slide surface 100 permits turning to and fro with low friction, without the risk of the spring fingers 44 being bent.

In an embodiment of the impression cap with a flat base surface 80, as is shown in FIG. 11, the free ends of the spring fingers 44 can be conical or wedge-shaped in order to permit an automatic bending of the spring fingers 44 radially inward when the impression cap 72 is fitted. A position coding on the outside of the impression cap 72, for example by means of a notch or a color marking, can make it easier to mount the impression cap 72 in approximately the correct position of rotation.

If the impression cap 72 is mounted on the tooth implant 10 or the secondary part 40 in a manner offset by 180° from the correct position of rotation, the narrower spring finger 44 snaps into the wider recess 84, while the other and wider spring finger 44 cannot engage in the narrower recess 84. In this case, the mounted impression cap 72 can still be turned to and fro to a limited extent, which is no longer the case when the impression cap 72 is correctly fitted. It is withdrawn again and mounted once more in approximately the correct position of rotation.

An impression cap 72 which can be mounted exclusively in the correct position of rotation on the tooth implant 10 provided with the secondary part 40 is shown in FIGS. 16 to 19. Following the base surface 80, the receiving space 78 has a circular cylindrical cross section along approximately half its depth measured in the direction of the longitudinal axis 22. This is indicated by B in FIGS. 16 and 17. Following this area, the clearance of the receiving space 78 is reduced by a step-shaped thickening of the wall 76. This is indicated by A in FIGS. 16 and 17. However, the thickened wall 76 has grooves 102 extending in the direction of the longitudinal axis 22 and corresponding to the different widths of the spring fingers 44. The bottom of these grooves 102 is at a distance from the central longitudinal axis 22 corresponding to the clearance of the recess 84 in the cylindrical area B. These grooves 102 lead into the corresponding recesses 84.

In this embodiment, the impression cap 72 can be pushed in any desired position of rotation over the spring fingers 44 of the secondary part 40 in the joining direction F until they come to the shoulder A. By turning the impression cap 72 while pressing slightly in the joining direction F, it is possible to find the correct position of rotation in which both spring fingers 44 can slide into their associated grooves 102. The snap-in lugs 60' snap automatically into the respective recesses 84 as soon as the impression cap 72 bears at least more or less completely on the shoulder 24 of the tooth implant 10, or on the support surface 96 in an embodiment of the secondary part 40 according to FIG. 10. In the embodiment of the impression cap shown in FIGS. 16 to 19, it is not only the snap-in lugs 60 that serve to secure against twisting; the spring fingers 44 are also received, along about half their length, in the associated grooves 102, which further improves the stability of the securing of the impression cap 72 compared to the previous embodiment.

Another embodiment of the secondary part 40 and of the impression cap 72 which permits only an unambiguous relative position of rotation is shown in FIGS. 20 to 23. The secondary part 40, otherwise of the same design as described above, has four fingers distributed about the circumference, of which two adjacent fingers are designed as spring fingers 44 with snap-in lugs 60 and the other two fingers 44', measured in the direction of the longitudinal axis 22, are only approximately half as long and are designed without snap-in lugs.

Figure 20:
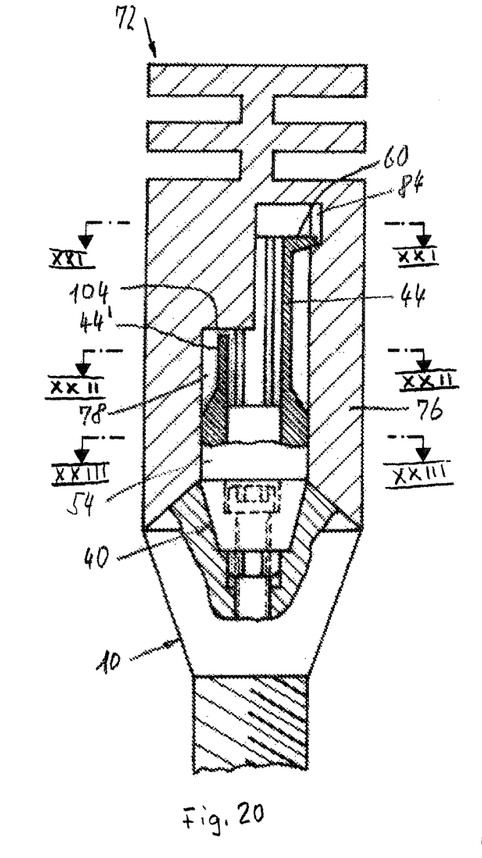
FIG. 20 shows, in a similar view to FIGS. 8 and 11, a device according to the invention with another embodiment of a secondary part and a matching impression cap.
Figure 21:
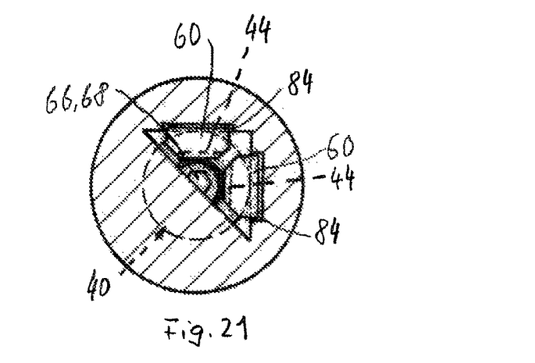
FIG. 21 shows a section through the device along the line XXI-XXI in FIG. 20.
Figure 22:
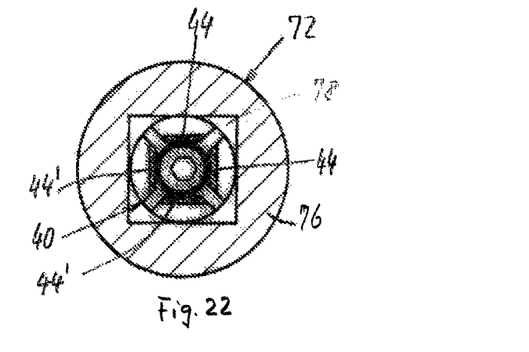
FIG. 22 shows a section through the device along the line XXII-XXII in FIG. 20.
Figure 23:
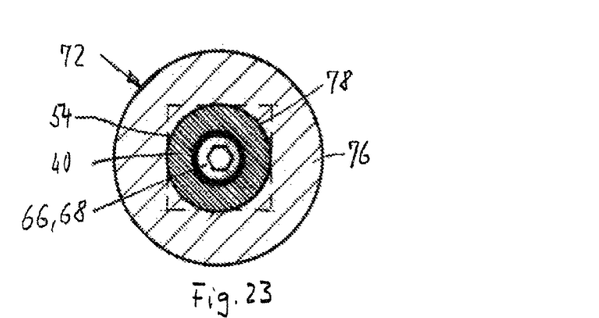
FIG. 23 shows a section through the device along the line XXIII-XXIII in FIG. 20.
Figure 24:
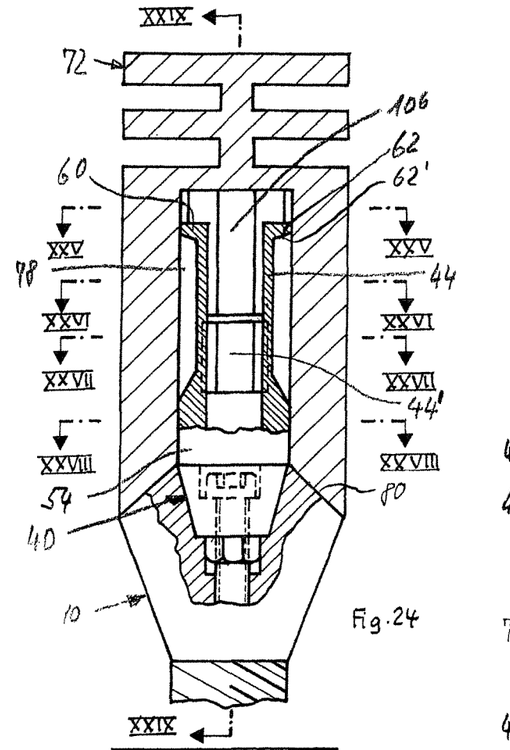
FIG. 24 shows, in a similar view to FIG. 20, another embodiment of the device according to the invention.

The corresponding impression cap 72, likewise shown in FIGS. 20 to 23, has a receiving space 78 with a circular cross section in that area in which it cooperates with the guide portion 54 of the secondary part 40, as can be seen in particular from FIG. 23. This area with a circular cross section extends along approximately a quarter to a third of the axial length of the receiving space 78. The cross section of the receiving space 78 then merges into a square shape, as is shown in FIG. 22. From about the halfway point of length of the receiving space 78, the cross section thereof corresponds to an equilateral right-angled triangle, the two sides lying in the same planes as the associated sides of the square cross section (see in particular FIG. 21). The transition of the cross section of the receiving space 78 from the square shape to the triangular shape forms an abutment surface 104 which allows the impression cap 72 to be lowered fully to the shoulder 24 of the tooth implant 10, or to the support surface 96 in the case of a design of the secondary part 40 according to FIG. 10, only when the impression cap 72 is in the correct position of rotation in relation to the secondary part 40, otherwise the spring fingers 44 or one of the spring fingers 44 with snap-in lug 60 bear on the abutment surface 104. Of course, the length of the spring fingers 44 without snap-in lug 60 and the position of the abutment surface 104 are adapted to each other in such a way that, in the correct position of rotation of the impression cap 72, complete assembly is permitted and a gap is still present between the fingers 44' and the abutment surface 104.

In the embodiment of the impression cap 72 shown in FIGS. 20 to 22, it is of course also possible to give the receiving space 78 a square cross section from the base surface 80 as far as the abutment surface 104, as is indicated by broken lines in FIG. 23. Here, as in the other embodiments too, the impression cap 72 bears with its wall 76 on the guide portion 54 in the assembled state.

Another device according to the invention in which the impression cap 72 can be mounted only in a single position of rotation is shown in FIGS. 24 to 29. The secondary part 40, otherwise of the same design as described above, has, like the embodiment shown in FIGS. 20 to 23, four fingers arranged in a cross shape. In the present embodiment, however, two spring fingers 44 lying opposite each other are designed with snap-in lugs 60. The two other fingers 44' have no snap-in lugs and, measured in the direction of the longitudinal axis 22, are shorter than the spring fingers 44 with snap-in lug 60 and are of different length, as can be seen particularly in FIG. 29. Moreover, the two fingers 44' without snap-in lugs 60 are more solid in cross section (see FIG. 27), since they do not have to be designed to be elastically bendable. Of course, these fingers 44' could have the same cross section as the other two spring fingers 44 with the snap-in lugs 60.

Figure 27:
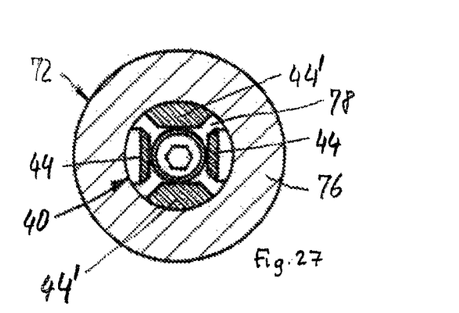
FIG. 27 shows a section through the device along the line XXVII-XXVII in FIG. 24.
Figure 28:
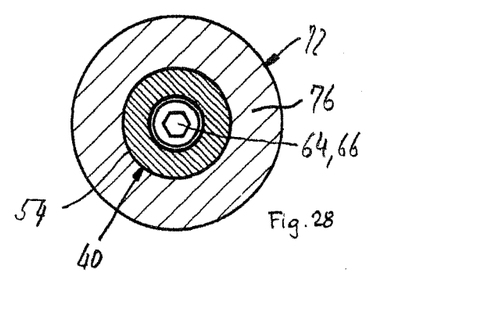
FIG. 28 shows a section through the device along the line XXVIII-XXVIII in FIG. 24.
Figure 29:
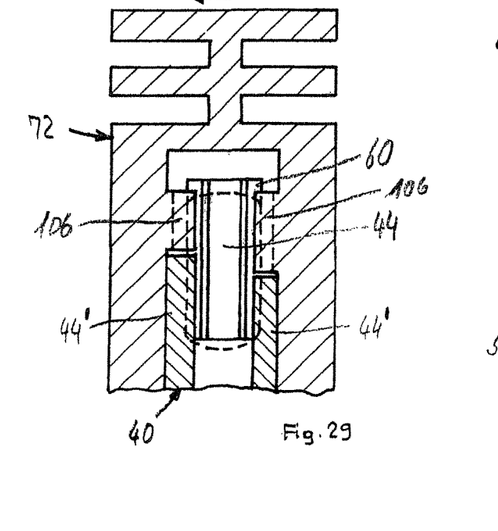
FIG. 29 shows a part of the device from FIG. 24 in a longitudinal section along the line XXIX-XXIX in FIG. 24.

The receiving space 78 of the impression cap 72 has a circular cylindrical cross section from the base surface 80 as far as longitudinal ribs 106, as is also shown in particular in FIGS. 27 and 28. Seen in the direction of the longitudinal axis 22, the receiving space 78 continues with the same cross section, but now two longitudinal ribs 106 lying opposite each other protrude radially inward (see in particular FIGS. 26 and 29). The end of the two longitudinal ribs 106 directed toward the base surface 80 is adapted to the length of the two fingers 44' without snap-in lug 60, in such a way that the impression cap 72 can be lowered completely in the direction of the tooth implant 10 only in the correct position of rotation and, in the final assembled state, a gap is left free between these fingers 44' and the longitudinal ribs 106. The spring fingers 44 with snap-in lug 60 find space between the longitudinal ribs 106.

Figure 25:
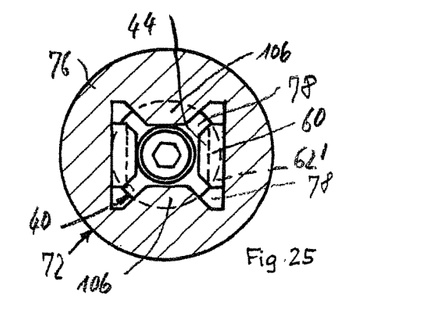
FIG. 25 shows a section through the device along the line XXV-XXV in FIG. 24.
Figure 26:
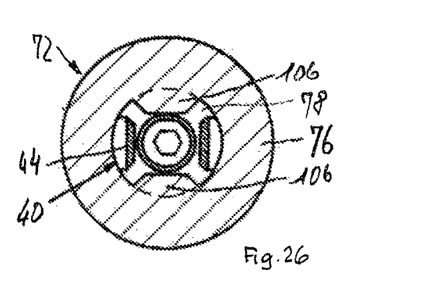
FIG. 26 shows a section through the device along the line XXVI-XXVI in FIG. 24.

The support faces 62 and the receiving spaces 78 for the snap-in lugs 60 are formed by a transition from the substantially circular cross section of the receiving space 78 to a square cross section, in which area the longitudinal ribs 106 protrude radially inward in relation to the square cross section, as is shown particularly clearly in FIG. 25. In the present embodiment, as also in the one according to FIGS. 20 to 23, the snap-in lugs 60 are advantageously straight at their radially outer free edge, as is shown clearly in FIGS. 21 and 25.

Also in the embodiment of the device according to the invention as shown in FIGS. 24 to 29, the mounting of the impression cap 72 on the tooth implant 10 provided with the secondary part 40 is possible only in a single position of rotation.

Figure 30:
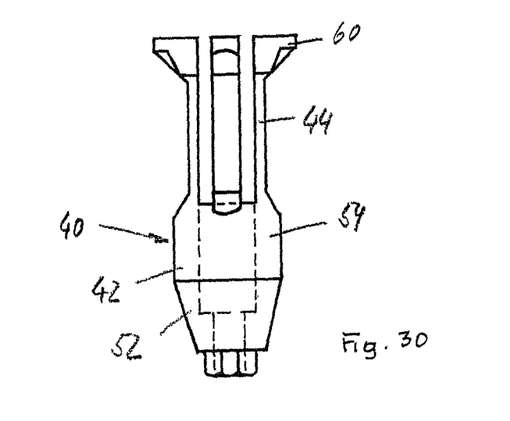
FIG. 30 shows a view of another embodiment of the secondary part.
Figure 31:
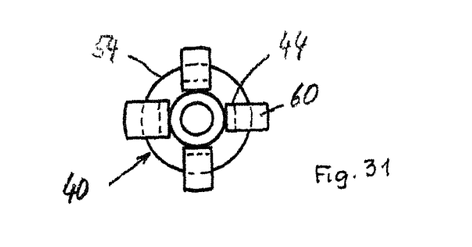
FIG. 31 shows a plan view of the secondary part according to FIG. 30.

FIGS. 30 and 31 show another embodiment of the secondary part 40 for a device according to the invention. It is very similar to the embodiment shown in FIGS. 4 to 6, the only difference being that, instead of two spring fingers 44, there are now four spring fingers 44 arranged in a cross shape, each with a snap-in lug 60. The corresponding impression cap 72 is the same as the one according to FIGS. 8 and 12 to 15, but four recesses 84 limited in the circumferential direction are now present for the four snap-in lugs 60. As is shown in FIG. 31, one of the spring fingers 44, and the associated snap-in lug 60, is wider than the other three spring fingers 44. As has been described above, this allows the impression cap 72 to be easily mounted on the tooth implant 10 provided with the secondary part 40, such that all four spring fingers 44 snap into the impression cap 72, only in a single position of rotation.

However, it will be expressly noted that all four spring fingers 44 with the snap-in lugs 60 can be identical, and all the corresponding recesses 84 can have the same shape. This allows the impression cap 72 to be mounted in four different directions of rotation. However, this is permissible in dentistry, since the position of rotation is already clear from the surrounding dentition, from the impression of the surrounding area of the dentition and from the master model/plaster model. The same also applies to the embodiments shown in FIGS. 1 to 19.

Accordingly, in the embodiments shown in FIGS. 20 to 29, it is also possible to provide four spring fingers 44 with snap-in lug 60 and to omit the change of cross section, in the embodiment in FIGS. 20 to 23, from square to triangular, and to omit the longitudinal ribs 106 in the embodiment according to FIGS. 24 to 28. In these cases too, the mounting of the impression cap 72 is then possible in four different positions of rotation, the exact position of rotation being ensured by the square cross section and the straight edge of the snap-in lugs 60. The number of possible positions of rotation of the impression cap 72 relative to the secondary part 40 is then half the number of possible positions of rotation of the secondary part 40 relative to the tooth implant 10.

It will also be noted that, in all the embodiments, the secondary part 40 can be designed with a support surface 96 corresponding to FIGS. 10 and 11, and all the impression caps in this case can be designed with a base surface 80 as shown in FIG. 11.

If the first positioning means 50 are hexagonal, instead of being octagonal as shown, secondary parts 40 with three spring fingers are recommended. Of course, the impression cap is then shaped correspondingly.

All of the embodiments shown prevent damage to, and permit optimal formation of, the mucous membrane, since the impression cap does not protrude radially from the tooth implant.

All of the embodiments shown have a snap-fit connection that can be released without destruction by overcoming a defined tensile force, the secondary part 40 always snapping actively.

The present invention is also applicable to devices in which the longitudinal axis of the tooth implant and the longitudinal axis of the impression cap are at an angle to each other.

The invention claimed is:

1. A combination comprising:
a device for securing an impression cap releasably on a tooth implant, the device comprising a secondary part having a base area that can directly be secured on the tooth implant by a screw connection and at least one spring finger integrally formed on the secondary part and protruding from the base area, and
an impression cap comprising a dimensionally stable wall peripherally delimiting a receiving space in the shape of a blind hole;
wherein the at least one spring finger extends into the receiving space to cooperate with the dimensionally stable wall of the impression cap to form a force fit attachment of the impression cap at the secondary part;
the spring finger having, in its free end area, a snap-in lug that cooperates with an undercut formed on the dimensionally stable wall of the impression cap wherein the undercut is formed on a recess in the impression cap which is limited in the circumferential direction such that it does not extend about the entire circumference of the impression cap and has, in the circumferential direction, an extent which corresponds to, or is only slightly greater than the extent of the snap-in lug and with which the snap-in lug engages in the assembled state in order to fix mutual position of rotation.

2. The combination as claimed in claim 1, wherein the spring finger and/or the undercut has a support face extending at an acute angle (α) with respect to an axial joining direction (F) in order to form a snap-fit connection that can be released by pulling.

3. The combination as claimed in claim 1, wherein the secondary part has an outer at least two spring fingers with the snap-in lug.

4. The combination as claimed in claim 1, wherein the base area has an outer surface which lies free in relation to the tooth implant and on which the dimensionally stable wall of the impression cap bears in an assembled state.

5. The combination as claimed in claim 1, further comprising a tooth implant, wherein the tooth implant is designed in one piece and has an anchoring portion, which is intended to be inserted in the jaw bone, and a head portion, which is intended to protrude above the jaw bone, and the head portion has a peripheral shoulder on which the impression cap, in an assembled state, bears via a base surface of at least approximately the same shape.

6. The combination as claimed in claim 5, wherein the peripheral shoulder is in the shape of a truncated cone.

7. The combination as claimed in claim 1, wherein a peripheral support surface is formed on the secondary part, on which support surface the impression cap bears, in an assembled state, via a base surface of at least approximately the same shape.

8. The combination as claimed in claim 1, wherein the base area comprises a through hole through which a screw can be inserted for directly securing the secondary part on the tooth implant.

9. The combination as claimed in claim 1, wherein the tooth implant and the secondary part have cooperating first positioning elements that mutually fix the position of rotation.

10. The combination as claimed in claim 9, wherein the cooperating first positioning elements have stub with a cross section of a regular polygon, and a recess of matching cross section.

11. The combination as claimed in claim 10, wherein the cross section is a regular, even-sided polygon.

* * * * *

UNITED STATES PATENT AND TRADEMARK OFFICE
CERTIFICATE OF CORRECTION

PATENT NO. : 9,326,832 B2  
APPLICATION NO. : 12/996137  
DATED : May 3, 2016  
INVENTOR(S) : Zucker et al.

Page 1 of 1

It is certified that error appears in the above-identified patent and that said Letters Patent is hereby corrected as shown below:

On the Title Page

In item (12) on the front of the patent, delete "Zuker et al." and insert --Zucker et al.--

In item (75) on the front of the patent, delete "Arik Zuker" and insert --Arik Zucker--

In the Claims

In column 12, line 2 (claim 1), before "mutual" insert --a--

In column 12, line 37 (claim 10), before "stub" insert --a--

Signed and Sealed this  
Twenty-eighth Day of June, 2016

Michelle K. Lee  
*Director of the United States Patent and Trademark Office*